United States Patent [19]

Schulz et al.

[11] 4,032,570

[45] June 28, 1977

[54] PROCESS FOR CONVERTING BUTANE TO ACETIC ACID

[75] Inventors: Johann G. D. Schulz, Pittsburgh, Pa.; Richard Seekircher, North Bay, Canada

[73] Assignee: Gulf Research & Development Company, Pittsburgh, Pa.

[22] Filed: July 23, 1975

[21] Appl. No.: 598,426

Related U.S. Application Data

[63] Continuation-in-part of Ser. No. 196,732, Nov. 8, 1971, abandoned, which is a continuation-in-part of Ser. No. 821,096, May 1, 1969, abandoned.

[52] U.S. Cl. .................. 260/533 R; 260/597 R
[51] Int. Cl.² ............................ C07C 51/20
[58] Field of Search .................. 260/533 R, 597 R

[56] References Cited

FOREIGN PATENTS OR APPLICATIONS 709,674   6/1954   United Kingdom .......... 260/533 R Primary Examiner—Vivian Garner

[57] ABSTRACT

A process for converting butane to acetic acid which comprises subjecting butane to reaction with a gas containing molecular oxygen in a lower fatty acid, in the presence of a cobalt compound soluble in the reaction medium while maintaining water in the reaction mixture throughout the reaction period until the termination of the reaction.

9 Claims, No Drawings

PROCESS FOR CONVERTING BUTANE TO ACETIC ACID

This application is a continuation-in-part application of our application Ser. No. 196,732, filed Nov. 8, 1971 for PROCESS FOR CONVERTING BUTANE TO ACETIC ACID which, in turn, is a continuation-in-part application of our application Ser. No. 821,096, filed May 1, 1969 for PROCESS FOR CONVERTING BUTANE TO ACETIC ACID, both now abandoned.

BACKGROUND OF THE INVENTION

1. Field of the Invention

This invention relates to a process for converting butane to acetic acid.

2. Description of the Prior Art

Processes for the oxidation of butane to acetic acid are known, but, invariably, such processes require excessively high temperatures and result in an oxygenated product mixture containing not only varying quantities of acetic acid but also oxygenated compounds including additional acids, such as formic acid, propionic acid and butyric acid; ketones, such as methyl ethyl ketone; alcohols, such as methanol, ethanol and isopropanol; esters resulting from the reaction of such acids with such alcohols; aldehydes, such as formaldehyde; etc.

A process that would appear to be feasible at low temperatures, that is, a temperature as low as about 150° F. (65° C.) is described in U.S. Pat. No. 3,293,292 of Olivier et al, which issued Dec. 20, 1966, but the reaction requires that butane be oxidized in the presence of a relatively complex catalyst system that includes bromine, cobalt and manganese and the product obtained contains undesirable amounts of ester. Each of the specific examples in the Olivier et al patent, however, is carried out at a temperature of 350° F. (177° C.). Since the latter temperature is relatively high we have attempted to carry out the reaction at a much lower temperature, that is, at 212° F. (100° C.) but without success. Thus, we have subjected 156 grams of butane to a temperature of 212° F. (100° C.) and an oxygen pressure of 300 pounds per square inch gauge in the presence of 1.65 grams of cobalt acetate tetrahydrate, 1.65 grams of manganese acetate tetrahydrate, 1.65 grams of ammonium bromide and 278 grams of acetic acid for 275 minutes but found no evidence that a reaction had occurred British Pat. No. 709,674 attempts to oxidize a lower hydrocarbon in oxygen under such conditions that water formed as a product of oxidation is removed from the reaction mixture substantially as it is formed, but relatively low yields of desired acid are obtained and recycling of large amounts of unreacted hydrocarbon is required.

SUMMARY OF THE INVENTION

We have found, however, and surprisingly, that butane can be oxidized with a gas containing molecular oxygen solely in the presence of a cobalt compound soluble in the reaction mixture while maintaining water of reaction in the reaction mixture throughout the reaction period, that is, until termination of the reaction, to obtain a reaction product containing almost solely acetic acid. This is extremely surprising in light of the teaching of the prior art. Theoretically, it would be expected that carbon-to-carbon scission of one mol of butane could result in (1) two mols of acetic acid and one mol of water, (2) one mol of propionic acid, one mol of formic acid and one mol of water or (3) one mol of butyric acid and one mol of water. Removal of hydrogen from an internal carbon could result in one mol of methyl ethyl ketone and one mol of water. Interaction of such compounds would be expected to lead to additional undesired oxygenated compounds. Additionally, some unwanted oxidation results in the production of useless carbon monoxide and carbon dioxide. It is, therefore, surprising that by operation of our process under relatively mild temperature conditions, and with an exceedingly simple catalyst system, we can obtain a product that contains almost solely acetic acid. Although it is inevitable that some exceedingly small amounts of carbon monoxide, carbon dioxide and decomposition and/or polymerization products are also produced in the present process, only three additional oxygenated products are formed, propionic acid, normal butyric acid and lesser amounts of methyl ethyl ketone. Fortuitously, each of the latter three compounds are formed in small amounts and each is commercially attractive.

As noted, the only components needed in the reaction system to produce acetic acid are butane, an oxygen-containing gas, an inert reaction medium, which is preferably a lower fatty acid, and a cobalt compound soluble in the reaction mixture. To convert butane to acetic acid any gas containing molecular oxygen, such as oxygen itself or air, can be used. The amount of oxygen used is at least that amount stoichiometrically required to satisfy the reaction producing the acetic acid at any level of conversion wherein it is desired to terminate the reaction. Complete utilization of oxygen is desirable, but it may be possible to use amounts in excess of those stoichiometrically required, for example, from about 1.5 to about 20 molar excess.

Cobalt can be used in the form of any compound, preferably as a salt, soluble in the reaction mixture. Thus, the cobalt compound can be in the form of an inorganic compound or as an organic compound, for example, as a cobaltous or cobaltic chloride, sulfate, nitrate, acetate, propionate, butyrate, isovalerate, benzoate, toluate, terephthalate, naphthenate, salicylate, acetyl acetonate, etc. Of these we prefer to employ cobaltous or cobaltic acetate. The amount of cobalt compound employed can vary over a wide range corresponding, for example, to about 0.05 to about 25 percent by weight of cobalt based on the reaction medium, defined hereinafter, although for efficient conversion of butane in a shorter reaction time, about 0.5 to about 20 percent by weight of cobalt, preferably about 2.0 to about 10 percent by weight of cobalt, is used.

The reaction medium can be any inert material in which the cobalt compound is soluble, but is preferably a lower fatty acid having from two to four carbon atoms, such as acetic acid, propionic acid or normal butyric acid. Of these we prefer to employ acetic acid, since it is the desired product, and complicated and unnecessary separation procedures are thus avoided. If such separation procedures pose little or no problems to an operator it is obvious that other inert reaction media, such as benzene, carbon tetrachloride, benzoic acid, etc., can also be used, although it can still be said in such event that the reaction herein is being carried out in acetic acid medium since acetic acid is produced herein. The amount of reaction medium employed can be varied over a wide range as long as a substantially homogeneous liquid phase is present during the reaction that includes butane, reaction medium and catalyst. Thus, the weight ratio of reaction medium to butane can be from about 1:1000 to about 1000:1, preferably from about 1:10 to about 10:1.

The reaction conditions, as noted, are mild. For example, the temperature can be from about 150° to about 275° F. (about 65° to about 135° C.), preferably from about 200° to about 275° F. (about 93° to about 135° C.), but most preferably from about 200° to about 250° F. (about 93° to about 121° C.). Pressure does not affect the reaction and the only consideration thereof resides in employing sufficient pressure to maintain the desired liquid phase. A pressure of about 50 to about 1000 pounds per square inch gauge, preferably about 100 to about 400 pounds per square inch gauge, is sufficient. Reaction time, similarly, is not critical and is dependent merely upon the amount of conversion desired at the end of the reaction period. Thus, a reaction period of about 1 minute to about 20 hours, preferably about 10 minutes to about 3 hours can be used. An extremely attractive feature of the process described resides in the fact that at all levels of conversion, the product distribution remains substantially the same.

Although the reaction defined herein can be made to go without an initiator, in some cases in order to initiate the reaction and to reduce the induction period, about 0.1 to about 10 percent by weight, preferably about one to about five percent by weight, of a conventional initiator, such as aldehydes, ketones, peroxides or any compound capable of furnishing free radicals under the reaction conditions herein, examples of which are acetaldehyde, methyl ethyl ketone, benzoyl peroxide, t-butylhydroperoxide, ozone, etc., can be employed.

The desired reaction can be carried out in any suitable manner, batch or continuous, as long as intimate contact is maintained among the various components of the reaction system. Thus, in a batch system, the reaction medium, for example, acetic acid, butane and the cobalt compound, for example, cobaltous acetate, are placed in a closed reactor and the same is pressured to reaction pressure with oxygen. The mixture is then raised to reaction temperature while stirring. Additional oxygen is introduced into the reaction system to compensate for the oxygen taken up by the reaction. Reaction is discontinued at any time when it is desired to terminate the reaction but preferably when further oxygen absorption ceases. The reaction mixture, upon termination of the reaction, is brought to atmospheric pressure, withdrawn from the reaction zone and can be separated by distillation into desirable fractions, for example, at temperatures of about 100° to about 320° F. (about 38° to about 160° C.) and a pressure of about 14.7 pounds per square inch gauge.

In a continuous reaction, butane, oxygen, reaction medium and dissolved cobalt compound are passed upwardly through a reactor containing a sparger or an inert packing, such as Raschig rings or Berl saddles maintained at suitable temperature and pressure to obtain the desired conversion. The reaction mixture is removed from the top of the reaction zone, passed to a gas-liquid separator wherein unreacted and/or entrained butane unreacted oxygen and carbon monoxide and/or carbon dioxide are removed, and then to a fractionator wherein the reaction mixture is separated into its component parts. Acetic acid containing dissolved cobalt and some methyl ethyl ketone, is recycled to the reaction zone.

In each case, batch or continuous, water is maintained in the reaction mixture throughout the reaction period until the reaction is terminated. In other words all of the components, those added as well as those formed, are maintained in the reaction zone throughout the reaction period, and only upon termination of reaction is the reaction mixture removed from the reaction zone for recovery of its component parts.

The process can further be illustrated by the following.

EXAMPLE I

A number of runs were carried out in an autoclave having a capacity of about one liter wherein normal butane was subjected to the action of oxygen in the presence of a cobalt salt and methyl ethyl ketone as initiator, in acetic acid as a reaction medium. In Runs Nos. 1 and 2 the pressure was maintained by continuously introducing oxygen into the reactor and withdrawing unreacted oxygen therefrom. In Runs Nos. 3, 4, 5 and 6 oxygen was also used to maintain the pressure, but none was permitted to escape. Water of reaction was maintained in the reaction mixture throughout the reaction period. As oxygen was consumed additional oxygen was introduced to maintain the desired pressure level. At the end of the reaction period the reaction product was analyzed by gas chromatography. The results obtained are set forth in TABLE I.

TABLE I

| Run Number | 1 | 2 | 3 | 4 | 5 | 6 |
|---|---|---|---|---|---|---|
| Charge Data | | | | | | |
| Normal Butane, Grams | 172 | 185 | 196 | 196 | 199 | 171 |
| Acetic Acid, Grams | 322 | 345 | 350 | 350 | 350 | 301 |
| Methyl Ethyl Ketone, Grams | 28 | 28 | 25 | 25 | 25 | 20 |
| Co(OAc)$_2$ . 4H$_2$O, Grams | 25 | 25 | 25 | 25 | 25 | 20 |
| Conditions | | | | | | |
| Temperature, ° F. (° C.) | 203 (95) | 230 (110) | 230 (110) | 229 (110) | 268 (131) | 240 (115) |
| Pressure, Pounds Per Square Inch Gauge | 250 | 250 | 318 | 350 | 350 | 340 |
| Time, Hours | 3 | 4 | 4 | 1.5 | 2 | 3 |
| Product Data | | | | | | |
| Acetic Acid, Grams | 185 | 247.3 | 255 | 264 | 154 | 225.3 |
| Propionic Acid, Grams | 8.3 | 8.9 | 11.4 | 10.6 | 8.9 | 9.6 |
| Normal Butyric Acid, Grams | 5.1 | 4.3 | 9.1 | 10.6 | 10.0 | 6.3 |
| Methyl Ethyl Ketone Grams | 15 | 5.5 | 9.1 | 10.6 | 4.9 | 5.5 |
| Assorted Oxygenated Compounds, Grams | Trace | 4.4 | 2.6 | 6.0 | 1.3 | 3.6 |
| Water, Grams | 45.2 | 59.0 | 60.0 | 65.0 | 41.7 | 59.7 |
| Yield Data | | | | | | |
| Weight Percent Normal Butane Converted to Total Product | 67 | 88 | 77 | 85 | 52 | 52 |

TABLE I-continued

| Run Number | 1 | 2 | 3 | 4 | 5 | 6 |
|---|---|---|---|---|---|---|
| Mols Acetic Acid Formed Per Mol of Normal Butane Reacted | 1.46 | 1.46 | 1.48 | 1.55 | 1.35 | 1.58 |
| Pounds Acetic Acid Formed Per Mol of Normal Butane Reacted | 1.50 | 1.50 | 1.52 | 1.60 | 1.40 | 1.64 |
| Efficiency To Total Acids | 91 | 93 | 91 | 92 | 90 | 93 |
| Weight Percent Normal Butane Converted To CO and $CO_2$ | 5.7 | 3.4 | 5.1 | 5.0 | 5.9 | 4.8 |

The advantage of operating in accordance with our procedure is apparent from a study of the data in TABLE I. Note that in each run acetic acid was the predominant compound produced, and, in fact, efficiency to total acids, acetic, propionic and butyric, was over 90 percent. Note also that methyl ethyl ketone was present in lesser amounts than in the charge. As will be seen hereinafter, the amount of methyl ethyl ketone produced, if any, is very small.

EXAMPLE II

An additional series of runs was made at a temperature of 200° to 212° F. (93° to 100° C.) and oxygen pressure of 250 pounds per square inch gauge over a period of three to four hours. The runs were carried out in the same fashion as Runs Nos. 3, 4, 5 and 6 above. The results are tabulated below in TABLE II.

EXAMPLE III

Although each of the above runs was carried out in the presence of a small amount of methyl ethyl ketone this was done solely for the purpose of reducing the induction period. In each instance the reaction would have gone in the absence of methyl ethyl ketone but would have merely required a longer induction period.

This is illustrated by Runs Nos. 12 and 13, whose data appear in TABLE III below. In Run No. 12, which was carried out in accordance with the procedure of Runs Nos. 1 and 2 above, no methyl ethyl ketone was employed. In Run No. 13, which was carried out in accordance with procedure used in Runs Nos. 3 through 11, inclusive, butane was subjected to oxidation solely in the presence of oxygen and 357 grams of the total reaction product obtained from Run No. 12.

TABLE II

| Run Number | 7 | 8 | 9 | 10 | 11 |
|---|---|---|---|---|---|
| Charge Data | | | | | |
| Normal Butane, Grams | 168 | 187 | 178 | 135 | 185 |
| Acetic Acid, Grams | 303 | 346 | 347 | 380 | 345 |
| Methyl Ethyl Ketone, Grams | 24.4 | 30.1 | 30.0 | 28.9 | 28.0 |
| $Co(OAc)_2 \cdot 4H_2O$, Grams | 0.3 | 1.7 | 5.0 | 25.0 | 25.0 |
| Weight Percent Cobalt Based on Acetic Acid | 0.023 | 0.116 | 0.34 | 1.56 | 1.72 |
| Product Data | | | | | |
| Acetic Acid, Grams | 15.8 | 100 | 112 | 150 | 247 |
| Propionic Acid, Grams | 1.3 | 2.7 | 5.0 | 7.3 | 8.9 |
| Normal Butyric Acid, Grams | 0.6 | 2.9 | 3.4 | 5.9 | 4.3 |
| Methyl Ethyl Ketone, Grams | 18 | 18 | 19 | 7.8 | 5.5 |
| Assorted Oxygenated Compounds, Grams | Trace | Trace | 6.2 | 1.7 | 4.4 |
| Water, Grams | 5.6 | 21 | 31.4 | 45.5 | 59.0 |
| Yield Data | | | | | |
| Weight Percent Normal Butane Converted to Total Product | 6.7 | 31.5 | 40.8 | 70.0 | 86.0 |
| Mols Acetic Acid Formed Per Mol of Normal Butane Reacted | 1.35 | 1.45 | 1.49 | 1.50 | 1.46 |
| Pounds Acetic Acid Formed Per Mol of Normal Butane Reacted | 1.40 | 1.50 | 1.53 | 1.54 | 1.51 |
| Efficiency To Total Acids | 84 | 91 | 86 | 86 | 93 |
| Weight Percent Normal Butane Converted to CO and $CO_2$ | 1.1 | 3.1 | 3.4 | 4.7 | 3.4 |

From the data in TABLE II it can be seen that at other levels of conversion excellent yields of desired products are obtained, although increased conversions are obtained with higher levels of cobalt concentration.

The total reaction product contained 314 grams of acetic acid, 2.3 grams of propionic acid, 1.5 grams of normal butyric acid, 16.1 grams of the cobalt salt, 0.8 gram of methyl ethyl ketone, 1.7 grams of unidentified oxygenated compounds and 20.6 grams of water. The results are tabulated below in TABLE III.

TABLE III

| Run Number | 12 | 13 |
|---|---|---|
| Normal Butane, Grams | 197 | 144 |
| Acetic Acid, Grams | 360 | (357 grams of product from (Run No. 12) |
| Methyl Ethyl Ketone, Grams | None | |
| $Co(OAc)_2 \cdot 4H_2O$, Grams | 25 | |

TABLE III-continued

| Run Number | 12 | 13 |
| --- | --- | --- |
| Conditions | | |
| Temperature, °F. (°C.) | 212(100° C.) | 240(115° C.) |
| Pressure, Pounds Per Square Inch Gauge | 250 | 350 |
| Time, Hours | 53 | 2.5 |
| Product Data | | |
| Acetic Acid, Grams | 127.2 | 192.8 |
| Propionic Acid, Grams | 3.6 | 5.0 |
| Normal Butyric Acid, Grams | 2.4 | 6.6 |
| Methyl Ethyl Ketone, Grams | 1.3 | 4.0 |
| Assorted Oxygenated Compounds, Grams | 2.7 | 1.0 |
| Water, Grams | 28.1 | 74.3 |
| Yield Data | | |
| Weight Percent Normal Butane Converted to Total Product | 37.5 | 82.0 |
| Mols Acetic Acid formed Per Mol of Normal Butane Reacted | 1.63 | 1.52 |
| Pounds of Acetic Acid Formed Per Mol of Normal Butane Reacted | 1.68 | 1.57 |
| Efficiency to Total Acids | 93 | 86 |
| Weight Percent Normal Butane Converted to CO and $CO_2$ | 2.1 | 9.5 |

The above data clearly illustrate that the reaction defined herein requires no initiator. Thus, in Run No. 12, no initiator was used and yet efficiency to total acids was 93 percent. Of the 53-hour period employed the induction period amounted to 42 hours. The reaction was permitted to go for 11 hours after induction, but it is believed that reaction had ceased well prior to the end of such period. Note, too, that in Run No. 12 an exceedingly small amount of methyl ethyl ketone was obtained. That the large amounts of methyl ethyl ketone employed in previous runs is not required, even when an initiator is used, is apparent from Run No. 13, wherein only 0.8 gram of methyl ethyl ketone was present, and reaction was terminated in 2.5 hours.

Obviously, many modifications and variations of the invention, as hereinabove set forth, can be made without departing from the spirit and scope thereof, and therefore only such limitations should be imposed as are indicated in the appended claims.

We claim:

1. A liquid-phase process for converting butane to a product predominating in acetic acid which comprises contacting butane with a gas containing molecular oxygen in the presence of a lower fatty acid and a cobalt compound soluble in the reaction mixture in amounts corresponding to about 0.5 to about 20 percent by weight of cobalt, based on said lower fatty acid, at a temperature of about 200° to about 250° F., said cobalt compound being the effective catalyst employed and containing solely cobalt as the metallic component, while maintaining in the reaction zone all of the components of the reaction mixture, including the water of reaction, throughout the reaction period until termination of the reaction.

2. The process of claim 1 wherein the amount of said cobalt is from about 2.0 to about 10 percent by weight.

3. The process of claim 1 wherein said cobalt compound is a cobalt salt.

4. The process of claim 1 wherein said cobalt compound is cobalt acetate.

5. The process of claim 1 wherein said lower fatty acid has from two to four carbon atoms.

6. The process of claim 1 wherein said lower fatty acid is acetic acid.

7. The process of claim 1 wherein the weight ratio of the lower fatty acid to butane is from about 1:1000 to about 1000:1.

8. The process of claim 1 wherein the weight ratio of the lower fatty acid to butane is from about 1:10 to about 10:1.

9. The process of claim 1 wherein the lower fatty acid is acetic acid, the cobalt compound is cobalt acetate and the weight ratio of acetic acid to butane is from about 1000:1 to about 1:1000.

* * * * *